United States Patent [19]

Kanner et al.

[11] 4,395,564
[45] Jul. 26, 1983

[54] PROCESS FOR THE PREPARATION OF ALKOXYHYDRIDOSILANES

[75] Inventors: Bernard Kanner, West Nyack; Steven P. Hopper, Mahopac, both of N.Y.

[73] Assignee: Union Carbide Corporation, Danbury, Conn.

[21] Appl. No.: 397,815

[22] Filed: Jul. 13, 1982

[51] Int. Cl.³ .......................... C07F 7/08; C07F 7/10; C07F 7/18
[52] U.S. Cl. ...................................................... 556/470
[58] Field of Search ........................................ 556/470

[56] References Cited

PUBLICATIONS

Bazant et al., "Organosilicon Compounds", vol. 1, Academic Press, N.Y., (1965), p. 86.

Primary Examiner—Paul F. Shaver
Attorney, Agent, or Firm—Paul W. Leuzzi, II

[57] ABSTRACT

A process whereby silanes of the general formula:

$$HSi(NRR')_x(R'')_{3-x}$$

wherein R, R' and R'' are independently an aliphatic or aromatic, substituted or unsubstituted, saturated or unsaturated hydrocarbon radical having from one to eight carbon atoms, inclusive and R and R' may also be hydrogen and where R'' may also be alkoxy and where x has a value from one to three are reacted in the presence of a catalyst with alcohols in the stoichiometry of approximately one equivalent of alcohol per mole of silicon-nitrogen bond to give unexpectedly high yields of alkoxyhydridosilanes. In the reaction the silyl amine groups have been replaced by alkoxide groups without significant loss of the silicon-hydrogen group. Similar reactions in the absence of a catalyst give undesirably low yields of the corresponding alkoxy silanes and, in most cases, substantial loss of silyl hydrogen groups.

14 Claims, No Drawings

PROCESS FOR THE PREPARATION OF ALKOXYHYDRIDOSILANES

CROSS-REFERENCE TO RELATED APPLICATIONS

The subject matter of this application is related to that of U.S. patent application Ser. No. 397,814, to Kanner et al. and filed on even date herewith, entitled: IMPROVED PROCESS FOR THE PREPARATION OF OXIMATOHYDRIDOSILANES AND AMINOXHYDRIDOSILANES.

BACKGROUND OF THE INVENTION

The preferential displacement of silicon-nitrogen bonds in a compound that additionally contains silicon-hydrogen bonds is unknown in the art. What is well known is the preferential displacement of silicon-chlorine bonds in a compound containing silicon-hydrogen bonds. This latter reaction is characterized by side reactions and massive amounts of hydrochloric acid byproduct. To overcome these problems a new process is needed.

The insertion of carbon dioxide into the silicon nitrogen bond to give silyl carbamates was initially studied in the early sixties. Originally it was proposed that the insertion was effected by the displacement of the amine by a carbamic acid derivative rather than a direct two atom insertion. However, it has been noted that trisilylamine and methyldisilylamine do not appear to react with carbon dioxide. Surprisingly, the present process differs from the large body of published work in that one to three amino groups may be displaced from silicon and the displacement occurs from a silane bearing a silicon hydrogen bond and that the silicon hydrogen bond is not attacked. Thus in this catalyzed process, the initial formation of a silylcarbamate linkage seems most reasonable. The silyl carbamate may be formed either by a direct two atom insertion by carbon dioxide or by the interaction of the silyl amine with a carbamate derivative. The greater reactivity of the silyl carbamate linkage versus a silyl amine linkage toward nucleophilic displacement by an alcohol leading to the formation of alkoxysilanes was noted in U.S. Pat. No. 3,792,073; U.S. Pat. No. 3,816,359; and U.S. Pat. No. 3,906,018.

In 1975 the reaction of N,O-bis-(trimethylsilyl)carbamate with alcohols, phenols and carboxylic acids was reported to lead to the formation of trimethylalkoxy (and acetoxy) silanes, carbon dioxide and ammonia. (L. Berkofer and P. Sommer, J. Organometal Chem., 99 (1975) Cl.). While the literature thus far cited is related to the process of this invention, the use of reactions of silyl carbamate linkages to carry out nucleophilic substitution reactions with alcohols with the retention of the labile silicon hydrogen linkage went unrecognized. In addition the catalyzed reactions described herein have a significant advantage over the currently taught and practiced art. For example, the commonly used method for the preparation of trialkoxysilane suffers from several disadvantages that can be circumvented by this invention. The current art is characterized by the following: (a) solvent is sometimes employed, (b) the reaction time is relatively long in order to minimize formation of tetra-alkoxysilanes and (c) hydrochloric acid is produced.

As the process is currently understood it appears to offer a new, convenient and high yield synthesis of alkoxysilanes and trialkoxysilanes in particular. It seems most likely that the process involves intermediate silyl carbamate linkages which appear to be enormously reactive toward displacement by alcohols when compared to silyl amine linkages or the silicon hydrogen bond.

The catalyzed process described here is clearly superior for the preparation of trialkoxysilanes in that it does not require solvent, it involves short reaction times and moderate temperatures, the displaced amine is much less corrosive than hydrogen chloride, and proceeds with remarkable and unexpected selectivity for the formation of trialkoxysilanes.

SUMMARY OF THE INVENTION

The instant invention provides a process for reacting silanes of the general formula:

$$HSi(NRR')_x(R'')_{3-x} \qquad I$$

wherein R, R' and R" may be aliphatic or aromatic, saturated or unsaturated, hydrocarbon radicals, substituted hydrocarbon radicals having from one to eight carbon atoms, inclusive, and R and R' may also be hydrogen and R" may also be alkoxy and x ranges from one to three, with alcohols of the general formula:

$$R'''OH \qquad II$$

wherein R''' is an aliphatic or aromatic, saturated or unsaturated, substituted or unsubstituted hydrocarbon radical having from one to twenty carbon atoms, inclusive, in the stoichiometry of approximately one equivalent of alcohol per mole of the silicon-nitrogen linkage in the presence of a catalyst. The reaction results in unexpectedly high yields of substituted silanes of the general formula I where the silyl amine groups have been replaced by alkoxide groups without significant loss of the silicon-hydrogen groups. Similar reactions in the absence of a catalyst result in undesirably low yields of the corresponding alkoxy silanes and, in most cases, very substantial loss of the silyl hydrogen. The critical aspect of the catalytic process is the virtually complete retention of the silicon hydrogen linkage in the product(s).

DETAILED DESCRIPTION OF THE INVENTION

In accordance with the present invention there is provided a novel reaction between the silanes of formula I and alcohols of formula II to provide alkoxyhydridosilanes in high yield.

The silanes generally believed to be useful in the process of the present invention are represented by the general formula:

$$HSi(NRR')_x(R'')_{3-x} \qquad (I)$$

wherein R, R' and R" are independently an aliphatic or aromatic, substituted or unsubstituted, saturated or unsaturated hydrocarbon radicals having from one to eight carbon atoms inclusive and where R and R' may also be hydrogen and where R" may also be alkoxy and where x has a value of from one to three. Preferably, R, R' and R" are independently an aliphatic, unsubstituted, saturated or unsaturated hydrocarbon radical having one to six carbon atoms, inclusive and x is two or three. Most preferably, the R and R' are each a methyl group and x is three.

Suitable silanes of formula I which may be employed in the invention process include, but are not limited to, dimethylaminomethylethylsilane, diethylamino-methylpropylsilane, methylaminomethylethylsilane, ethylaminomethylethylsilane, phenylaminomethylethylsilane, benzylaminomethylphenylsilane, diphenylaminomethylphenylsilane, dibenzylaminomethyl-phenylsilane, dimethylaminodimethylsilane, diethylaminodimethylsilane, methylaminodimethyl-silane, ethylaminodimethylsilane, diphenylaminodimethylsilane, dibenzylaminodimethylsilane, phenylaminodimethylsilane, benzylaminodimethylsilane, bis-dimethylaminomethylsilane, bis-diethylaminomethylsilane, bis-methylaminoethylsilane, bis-ethylaminoethylsilane, bis-diphenylaminomethylsilane, bis-benzylaminomethylsilane, bis-phenylaminomethylsilane, bis-benzylaminomethylsilane, bis-dimethylaminophenylsilane, bis-diethylaminophenylsilane, bis-ethylaminophenylsilane, bis-ethylaminopropylsilane, bis-diphenylaminopropylsilane, bis-dibenzylaminopropylsilane, tris-dimethylaminosilane, tris-diethylaminosilane, tris-methylaminosilane, tris-ethylaminosilane, tris-diphenylaminosilane, tris-dibenzylaminosilane, tris-phenylaminosilane, tris-benzylaminosilane, dicyclopentylaminomethylethylsilane, cyclopentylaminodimethylsilane, dicyclohexylaminodimethylsilane, cyclohexylaminodimethylsilane, bis-dicyclopentylaminomethylsilane, bis-cyclopentylaminomethylsilane, dicyclopentylaminodiphenylsilane, bis-dicyclopentylaminophenylsilane, tris-dicyclopentylaminosilane, cyclohexylaminodiphenylsilane, bis-cyclohexylaminomethylsilane, tris-cyclohexylaminosilane, tris(piperidino)silane and the like. Preferably the silane is tris(dimethylamino)silane.

The alcohols generally believed to be useful in the process of the present invention are represented by the general formula:

R'''OH       (II)

wherein R''' is an aliphatic or aromatic, substituted or unsubstituted, saturated or unsaturated hydrocarbon radical of from one to twenty carbons, inclusive. Preferably, R''' is an aliphatic, unsubstituted, saturated or unsaturated hydrocarbon radical of from one to six carbon atoms, inclusive and most preferably the alcohol is either methanol or ethanol. The process of the present invention should be understood to be capable of employing the alcohol in a pure state or in admixture with other alcohols.

It should be noted that more sterically demanding alcohols undergo reaction less readily and in some instances do not react in the absence of the catalyst. Examples of the alcohols which may be used in the above process include, but are not limited to, methanol, ethanol, n-propanol, i-propanol, n-butanol, i-butanol, t-butanol, cyclohexanol, phenol, benzyl alcohol, napthanol, 3-ethylhexan-1-ol, 3-ethylhexan-2-ol, menthol, cholesterol, 4-methylbenzyl alcohol, m-chlorophenol, isoamylalcohol, neopentylalcohol, 2-methylaminoethanol, 2-dimethylaminopropan-1-ol, nonanol, 2-methoxyethanol, 2-ethoxyethanol, 2-methyl-3-butyne-2-ol, 3-methyl-1-pentyne-3-ol, thioethanol and the like.

The process is a catalyzed one and the catalyst may be carbon dioxide, carbonoxy sulfide, carbon disulfide or amine complexes thereof. Some examples of amine complexes which are effective in the above process include, but are not limited to, dimethylammonium dimethylcarbamate, diethylammonium, diethylcarbamate, dipropylammonium dipropylcarbamate, dibutylammonium dibutylcarbamate, ammonium carbamate, methylammonium methylcarbamate, diphenylammonium diphenylcarbamate, phenylammonium phenylcarbamate, benzylammonium benzylcarbamate, dibenzylammonium dibenzylcarbamate, dimethylammonium diethylcarbamate, diethylammonium dimethylcarbamate, methylammonium ethylcarbamate, diphenylammonium dimethylcarbamate, dimethylammonium diphenylcarbamate, diethylammonium dibenzylcarbamate, dibenzylammonium diethylcarbamate, phenylammonium dimethylcarbamate, methylammonium diphenylcarbamate and the like.

In addition the following classes of catalysts may be employed to an equal or lesser advantage. Strong protic acids such as hydrohalic acids, for example hydrochloric acid, hydrobromic acid and hydroiodic acid; sulfuric acids, for example sulfuric acid and para-toluene-sulfonic acid; and others such as haloacetic acids for example trifluoroacetic acid. Lewis acids such as aluminum trichloride and ferric chloride may be used as a catalyst for the process to a lesser advantage than the catalysts listed above. In addition, certain carboxylic acids, such as acetic acid and its substituted derivatives, and salts derived therefrom, such as ammonium acetate, may be used as catalysts for the process.

The catalyst concentration employed in the instant process should be between about 0.01 to 10 mole percent of the silicon-nitrogen bonds sought to be esterified. It is preferred for the purpose of this invention to maintain the catalyst concentration between about 0.1 and 3 mole percent. Although higher and lower limits are possible no particular advantages are seen from higher, and thus costlier, concentrations and the lower concentrations may lead to some loss of the silicon-hydrogen linkage sought to be preserved.

The reaction conditions are such that the catalyzed reaction may be carried out with or without solvent. In most cases there is no particular advantage to utilizing a solvent. However, in cases where a solvent is desirable for some reason, such as solubility or temperature control, a solvent may be used. If a solvent is used, it should not contain an active hydrogen such as are found in alcohols and amines. Suitable solvents are exemplified by hydrocarbons or ethers such as hexane, toluene, diethylether, tetrahydrofuran and the like.

Additionally, the temperature is normally kept between 0° C. and 60° C. but the process could be run anywhere from −50° C. up to 150° C. and under special circumstances, perhaps higher. Due to the ease of the process there is no special advantage in operating at higher conditions of temperature.

The stoichiometry of the alcohol to the silicon-nitrogen linkage generally should not substantially exceed one in order to avoid substantial loss of the silyl-hydrogen linkage. Slight excess over stoichiometry may be desirable to keep the level of unreacted silicon-nitrogen groups to a minimum. In cases where it is desirable to prepare and isolate mixed aminoalkoxysilanes the stoichiometry of alcohol to silyl-amine linkage is generally less than one.

The order of addition of the reagents is important to the process described above. The reagents should be mixed in such a way as to avoid an excess of alcohol with respect to the silicon nitrogen linkage. It is therefore not advisable to add the aminosilane to the alcohol. Generally the catalyst is added to the silylamine or its solution prior to adding the alcohol but the catalyst may be present wholly or partially in the alcohol or its solution.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

The following abbreviations are used in the examples which follow:
TRIS: tris-dimethylaminosilane
DI-CARB: dimethylammonium dimethylcarbamate

Example 1—Reaction of TRIS with Three Equivalents of Ethanol in the Absence of Catalyst The "standard apparatus" for the series of examples was as follows: a three necked round bottomed 50 ml flask equipped with a magnetic stirring unit, constant pressure addition funnel and a reflux condenser topped with an inert gas inlet tube that had been flushed with an inert gas (nitrogen or argon). The flask was charged with 15.2 gm (94 mmol) of TRIS and the addition funnel was charged with 13.0 gm (282 mmol) of freshly opened absolute ethanol. The absolute ethanol was added dropwise with stirring under inert gas over a period of 60 minutes. An exothermic gas evolving reaction accompanied the addition. After cooling to room temperature the reaction mixture was analyzed by glpc and found to contain the following components by area percent (later work showed no significant difference in the results when analyzing by internal standard yield analysis): triethoxysilane (17.1%), TRIS (16.6%), tetraethoxysilane (66.0%). The products were identified by their glpc retention times.

These results clearly show that the reaction between TRIS and alcohols, especially ethanol, in the absence of a catalyst yields alkyl silicates in good yield. Similarly, the uncatalyzed reaction results in poor yields of alkoxyhydridosilanes.

Example 2-4—Reaction of TRIS with Three Equivalents of Ethanol in the Presence of DI-CARB These reactions were run in a manner identical to that described in Example 1 except that the catalyst was added to TRIS with stirring under nitrogen prior to the addition of the ethanol. Three levels of catalyst concentration were explored with the results reported as follows: approximate molar ratio of Si—N≡ to catalyst, % triethoxysilane, % TRIS and % tetraethoxysilane, respectively.
A. 300, 96, 0, 3
B. 600, 91, 0, 7
C. 1500, 53, 7, 38

Examples 5-8—Reaction of TRIS with One and Two Equivalents of Ethanol Catalyzed by DI-CARB and in the Absence of Catalyst These reactions were carried out in a fashion identical to that of Example 2 with a Si—N≡ to catalyst ratio of 300 except that the reaction mixture was analyzed after the addition of one equivalent and after the addition of two equivalents of ethanol. The results are reported as follows: Si—N≡ to catalyst molar ratio, number of equivalents of ethanol, % triethoxysilane, % TRIS, % tetraethoxysilane, respectively.
A. 300, 1, 39, 60, 1
B. 300, 2, 83, 15, 2
C. 0, 1, 17, 66, 17
D. 0, 2, 26, 36, 38

Example 9—Reaction of TRIS with Three Equivalents of Ethanol Catalyzed by Carbon Dioxide This reaction was carried out in a manner similar to Example 1 with the following exceptions. Carbon dioxide was bubbled through the ethanol used in this experiment at a vigorous rate for 5 minutes. The ethanol addition time was 15 minutes rather than 60 minutes. The reaction was run on a molar scale one half that of Example 1. Analysis of the reaction mixture indicated the presence of 95% triethoxysilane and 5% tetraethoxysilane.

Example 10—Reaction of TRIS with Three Equivalents of Methanol in the Absence of a Catalyst Carried out as described in Example 1 at one half the molar scale utilizing methanol that was degassed by bubbling nitrogen through the methanol for 15 minutes prior to sampling with the following results: trimethoxysilane (1.4%), TRIS (24%) and tetramethoxysilane (70%).

Example 11—Reaction of TRIS with Three Equivalents of Methanol in the Presence of DI-CARB Carried out as described in Example 2 at one half the molar scale with a Si—N≡ to catalyst molar ratio of 300 with the following results: trimethoxysilane (96%) and tetramethoxysilane (4%).

Example 12—Reaction of TRIS with Three Equivalents of Methanol in the Presence of Carbon Dioxide Carried out as described in Example 9 with the following results, trimiethoxysilane (93%) and tetramethoxysilane (7%).

Examples 13-21

The procedure followed as well as the results obtained for this series of Examples are fully set forth in Table I.

TABLE 1

| Example | Procedure of Example | Alcohol | % (RO)$_3$SiH | % Products (RO)$_4$Si | TRIS | Remarks |
|---|---|---|---|---|---|---|
| 13 | 10 | 1-PrOH | 47 | 40 | 13 | a |
| 14 | 11 | i-PrOH | 96 | 2 | — | b |
| 15 | 9 | i-PrOH | 97 | 2 | — | b |
| 16 | 10 | t-BuOH | — | — | 100 | |
| 17 | 11 | t-BuOH | 94 | — | — | c,d |
| 18 | 11 | t-BuOH | 100 | — | — | e |
| 19 | 9 | t-BuOH | 6 | — | 44 | f |
| 20 | 9 | t-BuOH | 23 | — | — | g |

TABLE 1-continued

| Example | Procedure of Example | Alcohol | % (RO)₃SiH | % Products (RO)₄Si | TRIS | Remarks |
|---|---|---|---|---|---|---|
| 21 | 9 | t-BuOH | 92 | — | — | d |

Remarks for Table 1
[a] Required heating at 80° C. for 20 minutes to complete consumption of the alcohol.
[b] Higher boiling component in about 2% yield was characterized by mass spectra as [(iPrO)₂SiH]₂O.
[c] Reaction heated at 60° C. for 3.5 hr. to consume alcohol.
[d] Yield based on isolated material 99.3% pure by area percent.
[e] Reaction utilized four times the normal catalyst amount and went cleanly to completion within 1 hr. of the start of the alcohol addition.
[f] Only one equivalent of alcohol used. In addition to the products indicated there was present (t-BuO) (Me₂N)₂SiH(3%) and (t-BuO)₂(Me₂N)SiH(41%) as determined by internal standard yield analysis.
[g] Only two equivalents of alcohol used. In addition to product indicated there was present (t-BuO) (Me₂N)₂SiH(1%) and (t-BuO)₂(Me₂N)SiH(60%) as determined by internal standard yield analysis.

Example 22—Reaction of Tris(dimethylamino)silane and a Two-fold Molar Excess of Tertiary Butanol Catalyzed by Carbon Dioxide, with Excess Carbon Dioxide and Additional Tertiary Butanol The standard apparatus was charged with 7.6 gm (47 mmol) of the silane and 7.0 gm (94 mmol) of tertiary butanol. A short burst of carbon dioxide served to initiate the reaction. After about 1 hour the reaction mixture was analyzed by internal standard yield analysis. The analysis utilized authentic TRIS, di-t-butoxydimethylaminosilane and tri-t-butoxysilane. The amount of t-butoxy-bis-dimethylaminosilane was estimated by area percent. Duplicate analysis gave the following distribution of products: TRIS (5.8%), t-butoxy-bis-dimethylaminosilane (1.0%), di-t-butoxydimethyolaminosilane (59.6%) and tri-t-butoxysilane (22.6%). Carbon dioxide was bubbled into the reaction mixture until the exothermic reaction had raised the temperature from 25° to 50° C. After cooling to room temperature the reaction mixture was analyzed giving the following distribution of products: TRIS (1.1%), t-butoxy-bis-dimethylaminosilane (2.0%), di-t-butoxydimethylaminosilane (31.5%) and tri-t-butoxysilane (25.0%).

The addition of 3.5 gm (47 mmol) of tertiary butanol caused an immediate exothermic reaction which raised the temperature to 50° C. The reaction mixture became cloudy. The internal standard yield analysis indicated the presence of 40.4 mmol (86%) of the tri-t-butoxysilane. The reaction mixture was allowed to stand overnight and it separated into two layers. The bottom layer of DI-CARB, 2.3 gm, identified by nmr, was removed using a transfer pipet. The upper layer was water white and weighed 15.7 gm. When corrected for the weight of internal standard, 3.75 gm. of hexamethyldisiloxane, the upper layer contained 11.95 gm (103%) of tri-t-butoxysilane.

Following the text of Example 11 the following additional examples were performed.

TABLE 2

| Example[a] | Catalyst | (RO)₃SiH | Products[b] (RO)₄Si | Others | Notes |
|---|---|---|---|---|---|
| 23 | Et₂NH₂⁺Et₂NCO₂⁻ | 91 | 9 | — | |
| 24 | n-Pr₂NH₂⁺n-Pr₂NCO₂⁻ | 95 | 5 | — | |
| 25 | n-Bu₂NH₂⁺n-Bu₂NCO₂⁻ | 95 | 5 | — | |
| 26 | C₅H₁₀NH₂⁺C₅H₁₀NCO₂⁻ | 98 | 2 | — | |
| 27 | CF₃CO₂H | 25 | 55 | 20 | c |
| 28 | HCl | 25 | 48 | 27 | c |
| 29 | H₂SO₄ | 34 | 44 | 22 | c |
| 30 | CH₃C₆H₄SO₃H | 30 | 47 | 23 | c |
| 31 | AlCl₃ | 34 | 39 | 27 | c |
| 32 | NH₄⁺AcO⁻ | 62 | 20 | 12 | d |
| 33 | AcOH | 81 | 12 | 7 | c,e |
| 34 | Me₂NH₂⁺Me₂NCO₂⁻ | 52 | 28 | 20 | f,g |
| 35 | Me₂NH₂⁺Me₂NCO₂⁻ | 70 | 14 | 16 | g,h |
| 36 | Me₂NH₂⁺Me₂NCO₂⁻ | 10 | 1 | 89 | i,j |
| 37 | MeNH₃⁺MeNHCO₂⁻ | 90 | 10 | — | |

Notes for Table 2
[a] The procedure of Example 11 was used with the exceptions indicated by notes.
[b] As determined by normalized area percent.
[c] The alcohol was added to the starting material, catalyst mixture over a period of about 1 hour.
[d] The standard catalyst loading was added both the alcohol in the addition funnel and to the reaction mixture. The addition time for this reaction was about 15 minutes.
[e] The standard catalyst loading was dissolved in the alcohol and omitted from the reaction flask.
[f] The alcohol addition was carried out with the reaction mixture held at −10° C. Analysis of the product mixture followed warming to room temperature.
[g] Methanol was used in place of ethanol.
[h] The alcohol addition was carried out with the reaction mixture held at 50° C. Analysis of the product mixture followed heating at about 80° C. for approximately 3 hours.
[i] Phenol was used in place of ethanol.
[j] The reaction mixture was heated to about 40° C. overnight before product analysis was performed.

Example 38—Reaction of Tris(dimethylamino)silane and Three Equivalents of Tertiary Butanol Catalyzed by Acetic Acid The "standard apparatus" was charged with 4.2 gm (26 mmole) of the silane and 5.8 gm (26 mmole) of tertiary butanol. Stirring under nitrogen was initiated and 0.048 gm (0.75 mmole) of glacial acetic acid was added to the stirred reaction mixture. The addition of the catalyst initiated a rapid, gas evolving, exothermic reaction which caused the temperature of the reaction mixture to increase from 24° to 57° C. over a period of roughly three minutes. The reaction mixture was sampled for glpc analysis at about 5 minutes after the addition of the catalyst. The analysis indicated the presence of tri-t-butoxysilane in greater than 90% yield based on starting silane.

Example 39—Reactions between Tris(piperidino)silane and Three Equivalents of Ethanol Catalyzed by Carbon Dioxide A round bottomed three necked 25 ml flask equipped with a magnetic stirring unit, a thermometer, constant pressure addition funnel and a reflux condenser topped with a nitrogen inlet tube was flushed with nitrogen.

The flask was charged with 3.5 gm of the title silane (12.4 mmol). With stirring under nitrogen 1.76 gm (37.3 mmol) of nitrogen sparged degassed ethanol was added over a period of 17 minutes. The exotherm of the reaction raised the contents of the flask from ambient temperature to 38° C. Analysis of the reaction mixture indicated by area percent (experimentally indistinguishable from internal standard yield analysis) a 78/22 distribution of tri/tetraethoxysilane. After one hour the latter ratio had dropped to 73/27 indicating a slow subsequent reaction at room temperature.

Example 40—Reaction Between Tris(piperidino)silane and Three Equivalents of Ethanol Utilizing Carbon Dioxide Enriched Ethanol The silane, 0.6 gm (2.1 mmole) was charged into a nitrogen filled test tube. To the test tube was then added 0.3 gm (6.3 mmole) of ethanol which had been sparged with carbon dioxide for 0.5 hour. The reaction mixture was stirred for twenty minutes after the evolution of gas had ceased. Analysis by glpc indicated the presence of piperidine, tri- and tetraethoxysilane. The normalized area percent of the latter two products was 74 and 26% respectively.

Example 41—Reaction Between Tris(piperidino)silane and Three Equivalents of Ethanol Catalyzed by Piperidylammonium Piperidylcarbamate The procedure of example 39 was utilized for the reaction of 4.0 gm (14.2 mmole) of the silane and 2.0 gm (42.6 mmole) of ethanol catalyzed by 0.1 gm of the title catalyst. Standard yield analysis indicated the presence of piperidine (88%), triethoxysilane (67%) and tetraethoxysilane (33%).

Example 42—Reaction Between Tris(piperidino)silane and Three Equivalents of Ethanol Catalyzed by Dimethylammonium Dimethylcarbamate The procedure of example 39 was used for the reaction of 3.5 gm (12.4 mmole) of the silane and 1.8 gm (37.4 mmole) of ethanol catalyzed by 50 microliters of the title catalyst. Standard yield analysis one hour after the completion of the addition indicated the presence of piperidine (90%), triethoxysilane (77%) and the tetraethoxysilane (23%).

Example 43—Reaction Between Tris(piperidino)silane and Tertiary Butanol Uncatalyzed and Catalyzed by Dimethylammonium Dimethylcarbamate A 25 ml, round bottomed, three necked flask equipped with a magnetic stirring unit, thermometer, constant pressure additon funnel and a reflux condenser topped with a nitrogen inlet tube was flushed with nitrogen. The flask was then charged with 3.4 gm (12.1 mmol) of the silane and 2.7 gm (36.3 mmol) of tertiary butanol. The reaction mixture was stirred at room temperature under nitrogen for twenty hours and analyzed by glpc. Analysis by area percent indicated the presence of tri-t-butoxysilane (identified by its retention time) 7.4% and the two intermediate substitution products (t-BuO)Si(H)(piperdino)$_2$ and (t-BuO)$_2$Si(H)(piperidino), 12.6% and 4.6% respectively. Dimethylammonium dimethylcarbamate, 48 microliters, was added to the stirred reaction mixture and the analysis was repeated after 0.5 hr. The glpc trace indicated the presence of piperidine and tri-t-butoxysilane both, presumably, in near quantative yield.

Example 44—Reaction Between Tris(dimethylamino)silane and Three Equivalents of 2-methyl-3-butyne-2-ol A 50 ml, round bottomed, three necked flask fitted with a magnetic stirring unit, constant pressure addition funnel, thermometer and a reflux condenser topped with a nitrogen inlet tube was flushed with nitrogen. The flask was charged with 6.9 gm (42.8 mmole) of the silane and 200 microliters of dimethylammonium diemthylcarbamate as a catalyst. The addition funnel was charged with 10.8 gm (128.3 mmole) of the title alcohol. The alcohol was added portionwise with stirring under nitrogen over a period of 46 minutes. The reaction mixture exothermed to 31° C. by the completion of the alcohol addition. The crude reaction mixture was rotary evaporated to yield 10.7 gm of crude product. Glpc examination of the crude isolated product showed a single peak with the retention time expected for the desired product and traces of higher boiling materials. The nmr spectrum of the crude product confirmed its identity as tris(2-methyl-3-butyne-2-oxy)silane via the following data: delta 4.76, s, 0.73H, Si—H; 2.39, s, 3.16H, —C≡CH and 1.56 ppm, s, 18.1 H, ≡C(CH$_3$)$_2$.

Example 45—Reaction Between Tris(dimethylamino)silane and Three Equivalents of 3-methyl-1-pentyne-3-ol The procedure of Example 44 was followed for the reaction between 6.8 gm (42.4 mmole) of the title silane and 12.4 gm (126.6 mmole) of the title alcohol. After rotary evaporation 13.8 gm of crude product was isolated which gave essentially one peak upon glpc analysis and was identified as tris(3-methyl-1-pentyne-3-oxy)silane by its nmr spectrum as follows: delta 4.82, s, 0.75H, Si—H, 2.39, s, 3.18H, —C≡CH; 1.89–1.48, s&q, 15.0H, —CH$_2$—C—CH$_3$ and 0.99 ppm, t, 9.03H, J=8H$^2$., —CH$_3$.

Example 46—Reaction Between Bis-(dimethylamino)methylsilane an Two Equivalents of Ethanol Catalyzed by Carbon Dioxide A 50 ml, round bottomed, three necked flask equipped with a magnetic stirring unit, gas dispersion tube and a reflux condenser topped with a nitrogen inlet tube was flushed with nitrogen and charged with 8.6 gm (65 mmole) of the silane. Carbon dioxide was bubbled into the silane which was cooled via an external wet ice bath at 8° C. The sparge tube was replaced with a constant pressure addition funnel which contained 6.12 gm (130 mmole) of ethanol. The ethanol was added with stirring under nitrogen over a period of 15 minutes. Examination by glpc of the reaction mixture 20 minutes after the completion of the addition indicated a near quantitative conversion to methyldiethoxysilane with traces of methyltriethoxysilane as a contaminant.

Examples 47 and 48—Reaction Between Tris(dimethylamino)silane and Three Equivalents of Tertiary Butanol The reaction between the reagents does not proceed in the absence of a catalyst. In the presence of the catalysts noted below the reaction between the reagents was shown to proceed to form tri-t-butoxysilane. In most cases the starting materials were consumed and the major product in moderate to good yield was tri-t-butoxysilane. The following catalysts have been demonstrated to be effective for the reaction: hydrochloric acid and trifluoroacetic acid. While all have yet to be demonstrated most, if not all, of the catalysts listed in Table 2 are expected to facilitate this reaction.

Example 49—Reaction of TRIS with equivalents of 2-methoxyethanol in the presence of DI-CARB The procedure of Example 44 was used for the reaction of 6.0 gm (37.2 mmole) of TRIS and 8.5 gm (111.6 mmol) of 2-methoxyethanol catalyzed by 100 microliters of DI-CARB. After the completion of the addition, which initiated a mildly exothermic, gas evolving reaction; the reaction mixture was tirred overnight. Examination of the crude reaction mixture by glpc indicated the presence of tri and tetra substituted product in a crude ration of 60 to 23. The nmr and i.r. spectra of the crude product mixture indicated the principle formation of tris (2-methoxyethoxy)silane as follows:

delta 4.12, s, 0.81H, Si—H; 3.72, t, 5.9H, $J=5H_2$, —O—$CH_2$— and 3.29/3.19, t/s, 15.3H, —$OCH_2$—/—$OCH_3$: i.r. Si—H=2220 cm$^{-1}$ Example 50—Reaction of TRIS with three equivalents of 2-Diisopropylaminoethanol in the presence of DI-CARB The procedure of Example 44 was used for the reaction of 5.2 gm (32.2 mmol) of TRIS and 14.0 gm (96.7 mmol) of 2-diisopropylaminoethanol catalyzed by 100 microliters of DI-CARB. After the completion of the addition, which initiated a mildly exothermic, gas evolving reaction, the reaction mixture was stirred overnight. The reaction mixture was found to contain as a principle product the expected tris(2-Diisopropylaminoethoxy)silane by the following nmr and i.r. data:

delta 4.26, s, 0.84H, SiH; 3.64, t, 5.9H, $J=8H_2$, —$OCH_2$—; 3.32–2.39, multiplits, 12.6H, —$CH_2$—N(CH=)$_2$ and 0.99 ppm, d, 35.6H, $_1J=7H_2$, =$CMe_2$. i.r. SiH=2250 cm$^{-1}$.

We claim:

1. A process for the preparation of alkoxyhydridosilanes which comprises reacting a silane of the general formula $$HSi(NRR')_x(R'')_{3-x}$$

wherein R, R' and R" are independently an aliphatic or aromatic, substituted or unsubstituted, saturated or unsaturated hydrocarbon radicals having from one to eight carbon atoms inclusive and where R and R' may also be hydrogen and where R" may also be alkoxy and where x has a value of from one to three with alcohols of the general formula $$R'''OH$$

where R''' is an aliphatic or aromatic, saturated or unsaturated, substituted or unsubstituted hydrocarbon radical having from one to twenty carbon atoms inclusive in the presence of a catalyst at a temperature between −50° C. to 150° C. where approximately one equivalent of alcohol is employed per mole of the silicon-nitrogen bond and where the catalyst concentration is equal to about 0.01 to 10 mole percent of the silicon-nitrogen bonds.

2. The process of claim 1 wherein R, R' and R" of the silane and R''' of the alcohol are independently an aliphatic, unsubstituted, saturated or unsaturated hydrocarbon radical having one to six carbon atoms inclusive.

3. The process of claim 1 wherein x of the silane is three.

4. The process of claim 1 wherein the reaction temperature is between 0° C. and 60° C.

5. The process of claim 1 wherein the catalyst concentration is between 0.1 and 3 mole percent of the silicon-nitrogen bonds.

6. A process for the preparation of alkoxyhydridosilanes which comprises reacting a silane of the general formula $$HSi(NRR')_x(R'')_{3-x}$$

with an alcohol of the general formula $$R'''OH$$

wherein R, R', R" and R''' are independently an aliphatic, saturated or unsaturated, unsubstituted, hydrocarbon radical having one to six carbon atoms inclusive and R and R' may also be hydrogen, x has a value of from one to three, in the presence of a catalyst at a temperature from −50° C. to 150° C. where the catalyst is present in an amount equal to from 0.01 to 10 mole percent of the silicon-nitrogen bond and there is approximately one equivalent of alcohol per mole of the silicon-nitrogen bond.

7. The process of claim 6 wherein R, R' and R" of the silane are each methyl groups.

8. The process of claim 7 wherein x is equal to 3.

9. The process of claim 6 wherein the alcohol is selected from the group consisting of methanal, ethanol, and 2-methoxyethanol.

10. The process of claim 6 wherein the temperature is between about 0° C. and 60° C.

11. The process of claim 6 wherein the catalyst concentration is between about 0.1 and 3 mole percent.

12. The process of claim 6 wherein the silane is tris(-dimethylamino silane), the alcohol is selected from the group consisting of methanol, ethanol, and 2-methoxyethanol the temperature is between about 0° C. to 60° C., the catalyst is dimethylammonium dimethylcarbamate and at a catalyst concentration of about 0.1 to 3.0 mole percent.

13. The process of claims 1 or 6 wherein the catalyst is carbon dioxide.

14. The process of claims 1 or 6 wherein the catalyst is acetic acid.

* * * * *